US

United States Patent [19]

Spatz

[11] Patent Number: 4,532,251
[45] Date of Patent: Jul. 30, 1985

[54] N-SUBSTITUTED-N',N'-DISUBSTITUTED GLYCINAMIDE FUNGICIDES

[75] Inventor: David M. Spatz, Fairfax, Calif.

[73] Assignee: Chevron Research Company, San Francisco, Calif.

[21] Appl. No.: 446,802

[22] Filed: Dec. 3, 1982

[51] Int. Cl.³ .................. A01N 43/36; A01N 43/38
[52] U.S. Cl. ............................ 514/354; 514/355; 514/423
[58] Field of Search ............... 546/316, 323; 548/537; 424/266, 274

[56] References Cited

FOREIGN PATENT DOCUMENTS 47-38426 9/1972 Japan .
48-37024 11/1973 Japan .

Primary Examiner—Henry R. Jiles
Assistant Examiner—Dale A. Bjorkman
Attorney, Agent, or Firm—S. R. LaPaglia; T. G. DeJonghe; S. L. Biggs

[57] ABSTRACT

The N-substituted-N',N'-disubstituted glycinamides of this invention are effective fungicides. In particular, they possess good activity against Bean Powdery Mildew.

8 Claims, No Drawings

N-SUBSTITUTED-N',N'-DISUBSTITUTED GLYCINAMIDE FUNGICIDES

BACKGROUND OF THE INVENTION

This invention is drawn to novel fungicides.

With the world more dependent for food on an ever decreasing amount of cultivated farmland, it is increasingly important to develop effective fungicides which protect crops from fungicidal destruction.

Kozlik et al, in CA 79:53327Z, disclosed 1-carbamoylimidazoles as insecticidal.

Brookes et al, in U.S. Pat. Nos. 4,080,462 and 3,991,071, disclosed 1-(N,N-disubstituted carbamoyl and thiocarbamoyl)-imidazoles as fungicidal.

Birchmore et al, in U.S. Pat. No. 4,250,179, disclosed complexes of a metal salt with N,N-disubstituted carbamoyl imidazoles (including some of those disclosed by Brookes et al) as fungicidal.

SUMMARY OF THE INVENTION

The compounds of the present invention are represented by the formula:

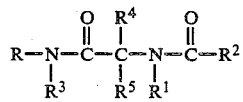

wherein R is phenyl, or phenyl substituted with 1 to 4 substituents independently selected from fluoro, chloro, bromo, iodo, nitro, lower alkyl, or trihalomethyl; $R^1$ is lower alkyl; $R^2$ is a 5- or 6-member heterocyclic ring containing 1 to 2 nitrogen atoms and the remainder of the ring atoms carbon atoms, with the proviso that a nitrogen of the 5- or 6-member heterocyclic ring is not bonded to the

group; and $R^3$, $R^4$ and $R^5$ are independently lower alkyl, or hydrogen.

Among other factors, the present invention is based on my finding that the compounds of this invention are effective fungicides. In particular, they possess good activity gainst Bean Powdery Mildew.

In part due to their superior fungicidal activity, preferred R groups include the trihalophenyl and dihalophenyl groups. Particularly preferred R groups are 2,4,6-trihalophenyl and 2,6-dihalophenyl.

Preferred halogens are chloro and bromo.

Preferred $R^1$ lower alkyl groups are n-propyl and ethyl.

Preferred $R^2$ groups include, for instance, 3-pyridyl, 5-pyrimidyl, 3-pyrazinyl, and 5-(1-methylimidazolyl).

Particularly preferred $R^2$ groups are the 6-member heterocycles containing 1 to 2 nitrogen atoms and include, for instance, 3-pyridyl, 5-pyrimidyl, 3-pyrazinyl, and the like.

Most preferably, $R^2$ is 3-pyridyl.

Preferably, $R^3$, $R^4$ and $R^5$ are hydrogen.

Definitions

As used herein, the following terms have the following meanings, unless expressly stated to the contrary.

The term "alkyl" refers to both straight- and branched-chain alkyl groups. Generally, such alkyl groups contain from 1 through 12 carbon atoms.

The term "lower alkyl" refers to both straight and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "a 6-member heterocyclic ring containing 1 to 2 nitrogen atoms" refers to the groups pyridyl, pyridazinyl, pyrimidyl, pyrazinyl, and the like.

The term "a 5-member heterocyclic ring containing 1 to 2 nitrogen atoms" refers to the groups imidazolyl, pyrrolyl, pyrazolyl, and the like.

The term "glycinamide" refers to the group:

with the nitrogen of the amino group referred to as the N'- group and the nitrogen of the amide referred to as the N- group. Thus, the term "N-(2,4,6-trichlorophenyl), N'-(n-propyl) glycinamide" refers to the group:

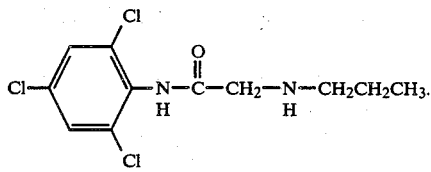

The term "N-(2,4,6-trichlorophenyl), N'-(n-propyl) N'-(3-pyridylcarbonyl)-α,α-dimethylglycinamide" refers to the group:

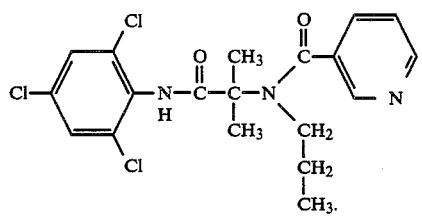

DETAILED DESCRIPTION OF THE INVENTION

The compounds of the present invention are conveniently prepared according to the following synthetic scheme:

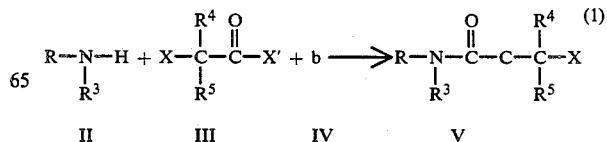

-continued

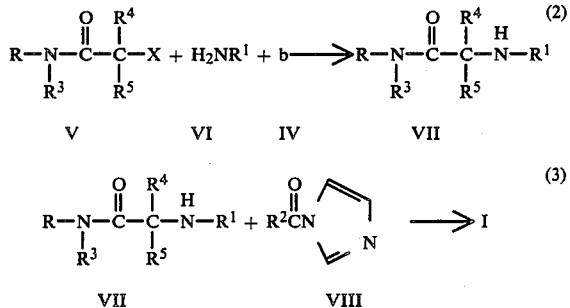

wherein R, R¹, R², R³, R⁴, and R⁵ are as above defined; X and X' are independently halogen; and b is a base.

Reaction (1) is conducted by adding an essentially equimolar amount of an α-haloacetyl halide, III, to II. The reaction is conducted in the liquid phase employing an aprotic anhydrous organic solvent such as chloroform, methylene chloride, toluene, and the like. An essentially equimolar amount of a base, IV, is added to the system to scavenge the acid generated during the reaction. Preferably, an organic base such as trialkylamine (e.g., triethylamine), pyridine, and the like, is employed. Reaction pressure is not critical and for convenience, is conducted at atmospheric pressure. The reaction is generally conducted at from $-20°$ C. to $80°$ C., although preferably at from $0°$ C. to $25°$ C., and is generally complete from within 1 to 24 hours. The resulting amide, V, is then isolated by conventional procedures such as extraction, filtration, chromatography, distillation, or alternatively, is used in Reaction (2) without purification and/or isolation.

Reaction (2) is conducted by adding an essentially equimolar amount of the appropriate primary amine, VI, to V. An essentially equimolar amount of a base, IV, is added to the system in order to scavenge the acid generated during the reaction. Preferably, an organic base such as trialkylamine (e.g., triethylamine), pyridine, and the like, is employed. The reaction is done in the liquid phase using an inert anhydrous organic solvent such as chloroform, methylene chloride, dimethoxyethane, and the like. Alternatively, in lieu of adding solvent and base, the reaction may be accomplished by using an excess amount of the primary amine, VI. Reaction pressure is not critical and for convenience, the reaction is generally conducted at atmospheric pressure. The reaction is generally conducted at from $0°$ C. to $100°$ C., although preferably at from $20°$ C. to $50°$ C., and is generally complete from within 1 to 24 hours. The product, VII, is isolated by conventional procedures such as extraction, filtration, chromatography, distillation, or alternatively, is used in Reaction (3) without purification and/or isolation.

Reaction (3) is conducted by first preparing reagent VIII. VIII is prepared by adding an essentially equimolar amount of carbonyldiimidazole to the appropriate acid, $R^2CO_2H$ wherein $R^2$ is as defined above. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from $0°$ C. to $100°$ C., although preferably at room temperature, and is generally complete from within 1 to 24 hours.

The resulting carboxylic acid imidazolide, VIII, may be isolated by conventional procedures such as extraction, filtration, chromatography, distillation, and the like. Alternatively and preferably, the reagent is not isolated from the reaction solution but an essentially equimolar amount of the amine, VII, is added to the system. Reaction pressure is not critical and for convenience, this reaction is generally conducted at atmospheric pressure. After addition of VII, the reaction is generally conducted at room temperature and is generally complete from within 1 to 24 hours. The product, I, is then isolated by conventional procedures such as extraction, filtration, chromatography, distillation, and the like.

Utility

The compounds of this invention are useful for controlling fungi, particularly leaf blights caused by *Septoria apii* and *Alternaria solani conidia*, and powdery mildew caused by *Erysiphe polygoni*.

However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry drust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition. The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperatures and temperature ranges refer to the Centigrade system and the term "ambient" or "room temperature" refers to about 20° C. to 25° C. The term "percent" refers to weight percent and the term "mole" or "moles" refers to gram moles. The term "equivalent" refers to a reagent equal in moles to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

Example 1

Preparation of α-bromo-N-(2,4,6-trichlorophenyl) acetamide 2,4,6-trichloroaniline, 49.1 gm, was added to 250 ml of methylene chloride. The system was cooled to 0° C. and 34.8 ml of triethylamine was then added. After addition of the triethylamine, 21.8 ml of bromacetylbromide was added. The system was allowed to warm to room temperature and stirred there for 18 hours. The reaction was then stopped and the solvent was washed with saturated sodium bicarbonate solution. The methylene chloride layer was separated and partially stripped when a solid precipitated from solution. The solid was filtered and air dried to yield 41.4 gm of α-bromo-(2,4,6-trichlorophenyl) acetamide as a gray solid.

Similarly, by following the procedure outlined above and using the appropriate starting material and reagents, the following are prepared:

α-chloro-α,α-dimethyl-N-(2,4,6-trichlorophenyl) acetamide;

α-bromo-N-(2,6-dichlorophenyl) acetamide;

α-chloro-N-(4-t-butylphenyl) acetamide;

α-chloro-N-(2,4,6-tribromophenyl) acetamide;

α-bromo-N-(2,6-dibromophenyl) acetamide;

α-bromo-N-[3,5-di-(trifluoromethyl)phenyl] acetamide;

α-bromo-N-methyl-N-(2,4,6-trichlorophenyl) acetamide; and

α-bromo-N-(2,4,6-trimethylphenyl) acetamide.

Example 2

Preparation of N-(2,4,6-trichlorophenyl)-N'-(n-propyl) glycinamide

α-bromo-N-(2,4,6-trichlorophenyl) acetamide, 41.4 gm, was added to 100 ml of n-propylamine. The system was heated at reflux for 16 hours. The reaction was then stopped and the excess n-propylamine was removed by stripping. The residue was dissolved in methylene chloride. The methylene chloride solution was washed with water. The remaining unreacted α-bromo-N-(2,4,6-trichlorophenyl) acetamide precipitated from solution and was then filtered. The methylene chloride was removed by stripping to give 15.1 gm, of N-(2,4,6-trichlorophenyl)-N'-(n-propyl) glycinamide.

Similarly, by following the procedure outlined in the above example and using the appropriate starting material and reagents, the following are prepared:

N-(2,4,6-tribromophenyl)-N'-(n-propyl) glycinamide;

N-(2,4,6-tribromophenyl)-N'-ethyl glycinamide;

N-(2,6-dichlorophenyl)-N'-ethyl glycinamide;

N-(4-t-butylphenyl)-N'-(n-propyl) glycinamide;

N-(2,4,6-trimethylphenyl)-N'-(n-propyl) glycinamide;

N-(4,6-dichlorophenyl)-N'-ethyl glycinamide; and

N-(4-nitrophenyl)-N'-ethyl glycinamide.

Example 3

Preparation of N-(2,4,6-trichlorophenyl), N'-(n-propyl), N'-(3-pyridylcarbonyl) glycinamide (a) 3-pyridine carboxylic acid, 2.5 gm, was added to 40 ml of methylene chloride. 3.2 gm of carbonyldiimidazole was added to the system. The system was stirred at room temperature for 18 hours to give the 3-pyridyl carboxylic acid imidazolide.

(b) N-(2,4,6-trichlorophenyl)-N'-(n-propyl) glycinamide, 5.9 gm, was then added to 3-pyridyl carboxylic acid imidazolide mixture of Step (a). The system was stirred at room temperature for 24 hours. The reaction was then stopped and the methylene chloride solution was washed with sodium bicarbonate solution and then with water. The methylene chloride solution was dried over magnesium sulfate and the methylene chloride removed by stripping to give 2.3 gm of the N-(2,4,6-trichlorophenyl), N'-(n-propyl), N'-(3-pyridylcarbonyl) glycinamide.

Similarly, by following the procedure outlined in the above example and using the appropriate starting material and reagents, the following are prepared:

N-(2,4,6-tribromophenyl)-N'-(n-propyl), N'-(5-pyrimidylcarbonyl) glycinamide;

N-(2,6-dibromophenyl)-N'-ethyl, N'-pyrazinylcarbonyl glycinamide;

N-(2,6-dichlorophenyl)-N'-ethyl, N'-(1-methyl-5-imidazolylcarbonyl) glycinamide;

N-(4-t-butylphenyl)-N'-(n-propyl), N'-(5-pyrimidylcarbonyl) glycinamide; and N-(2,6-dimethylphenyl)-N'-(N'-(n-propyl), N'-(3-pyridylcarbonyl) glycinamide.

Compounds made according to Examples 1 to 3 are shown in Table I.

Example A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

Example B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

Example C

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

Example D

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

Example E

Grape Downy Mildew

The compounds of the invention were tested for the control of the Grape Downy Mildew organism *Plasmopara viticola*. Detached leaves, between 70 mm and 85 mm in diameter, 7-week-old *Vitis vinifera* cultivar Emperor grape seedlings were used as hosts. The leaves were sprayed with a 250-ppm solution of the test compound in acetone. The sprayed leaves were dried, inoculated with a spore suspension of the organism, placed in a humid environmental chamber and incubated at 66° F. to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

Example F

Leaf Rust

The Leaf Rust test was made using pinto beans. The pathogen was *Uromyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F. to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

Example G

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a non-ionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greehouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 \times \left( \frac{\% \text{ disease in treated plants}}{\% \text{ disease in check}} \right)$$

The results are tabulated in Table II.

TABLE I

| Compound No. | Compound | ANALYSIS | | | | | | Form |
|---|---|---|---|---|---|---|---|---|
| | | Carbon | | Hydrogen | | Nitrogen | | |
| | | Calc. | Found | Calc. | Found | Calc. | Found | |
| 1 |  | 51.02 | 49.30 | 4.03 | 3.79 | 10.50 | 9.75 | oil |
| 2 |  | 70.12 | 68.68 | 7.13 | 7.57 | 12.91 | 13.22 | oil |

TABLE II

| Compound No. | Fungicidal Activity % Control | | | | | | |
|---|---|---|---|---|---|---|---|
| | GDM | TLB | CLB | TEB | BR | BPM | RB |
| 1 | 3 | 0 | 50 | 85 | 4 | 100 | 0 |
| 2 | 7 | 10 | 58 | 22 | 0 | 53 | 0 |

GDM — Grape Downy Mildew (*Plasmopara viticola*)
TLB — Tomato Late Blight (*Phytophthora infestans conidia*)
CLB — Celery Late Blight (*Septoria apii*)
TEB — Tomato Early Blight (*Alternaria solani conidia*)
BR — Bean Rust Eradicant (*Uromyces phaseoli tipica*)
BPM — Bean Powdery Mildew (*Erysiphe polygoni*)
RB — Rice Blast (*Piricularia oryzae*)

What is claimed is:

1. A fungicidal composition comprising a biologically inert carrier and a fungicidally effective amount of a compound of the formula

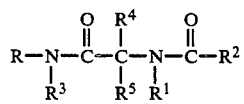

wherein R is dihalophenyl or trihalophenyl, R¹ is lower alkyl, R² is a 5- or 6-member aromatic heterocyclic ring containing one ring nitrogen and the remainder of the ring atoms carbon atoms, with the proviso that a nitrogen of the heterocyclic ring is not bonded to the $$-\overset{O}{\underset{\|}{C}}-$$

2. A fungicidal composition comprising a biologically inert carrier and a fungicidally effective amount of a compound of the formula defined in claim 1 wherein R² is pyridyl.

3. A fungicidal composition comprising a biologically inert carrier and a fungicidally effective amount of a compound of the formula defined in claim 1 wherein R is 2,4,6-trichlorophenyl, R¹ is n-propyl, and R² is 3-pyridyl.

4. A fungicidal composition comprising a biologically inert carrier and a fungicidally effective amount of a compound of the formula defined in claim 1 wherein R² is 3-pyridyl.

5. A method for controlling fungi which comprises contacting said fungi or their growth environment with a fungicidally effective amount of a compound of the formula

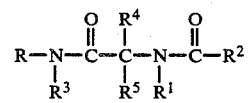

wherein R is dihalophenyl or trihalophenyl, R¹ is lower alkyl, R² is a 5- or 6-member aromatic heterocyclic ring containing one ring nitrogen and the remainder of the ring atoms carbon atoms, with the proviso that a nitrogen of the heterocyclic ring is not bonded to the $$-\overset{O}{\underset{\|}{C}}-$$

6. A method for controlling fungi which comprises contacting said fungi or their growth environment with a fungicidally effective amount of a compound of the formula defined in claim 5 wherein R² is pyridyl.

7. A method for controlling fungi which comprises contacting said fungi or their growth environment with a fungicidally effective amount of a compound of the formula defined in claim 5 wherein R is 2,4,6-trichlorophenyl, $R^1$ is n-propyl and $R^2$ is 3-pyridyl.

8. A method for controlling fungi which comprises contacting said fungi or their growth environment with a fungicidally effective amount of a compound of the formula defined in claim 5 wherein $R^2$ is 3-pyridyl.

* * * * *

UNITED STATES PATENT AND TRADEMARK OFFICE
CERTIFICATE OF CORRECTION

PATENT NO. : 4,532,251

DATED : July 30, 1985

INVENTOR(S) : DAVID M. SPATZ

It is certified that error appears in the above-identified patent and that said Letters Patent are hereby corrected as shown below:

Col.2, Line 64, "$\overset{O}{\underset{}{\|}}\text{-C-C-}\overset{R^4}{\underset{R^5}{|}}\text{-}$" should read -- $\overset{O}{\underset{}{\|}}\text{-C-}\overset{R^4}{\underset{R^5}{|}}\text{-}$ --.

Col.4, Line 48, "dry drust" should read -- dry dust --.

Col.9, Line 5, "greehouse" should read -- greenhouse --.

Claim 1, Col.10, Line 5, " $\overset{O}{\underset{}{\|}}\text{-C-}$ "

should read -- $\overset{O}{\underset{}{\|}}\text{-C-}$ group; and $R^3$, $R^4$, and $R^5$ are hydrogen. --

Claim 5, Col.10, Line 64, " $\overset{O}{\underset{}{\|}}\text{-C-}$ "

should read -- $\overset{O}{\underset{}{\|}}\text{-C-}$ group; and $R^3$, $R^4$, and $R^5$ are hydrogen. --

Signed and Sealed this

Twenty-seventh Day of May 1986

[SEAL]

Attest:

DONALD J. QUIGG

Attesting Officer

Commissioner of Patents and Trademarks